(12) United States Patent
Tanter et al.

(10) Patent No.: US 11,399,804 B2
(45) Date of Patent: Aug. 2, 2022

(54) ULTRASONIC METHOD AND DEVICE FOR CHARACTERISING WEAK ANISOTROPIC MEDIA, AND ULTRASONIC PROBE ASSEMBLY FOR SUCH A CHARACTERISATION DEVICE

(71) Applicants: Centre national de la recherche scientifique, Paris (FR); INSTITUT NATIONAL DE LA SANTE ET DE LA RECHERCHE MEDICALE (INSERM), Paris (FR); ECOLE SUPERIEURE DE PHYSIQUE ET DE CHIMIE INDUSTRIELLES DE LA VILLE DE PARIS, Paris (FR); UNIVERSITÉ PARIS DIDEROT—PARIS 7, Paris (FR)

(72) Inventors: Mickaël Tanter, Bagneux (FR); Mathieu Pernot, Paris (FR); Mathias Fink, Meudon (FR); Jean-Luc Gennisson, Cergy (FR)

(73) Assignees: CENTRE NATIONAL DE LA RECHERCHE SCIENTIFIQUE (C.N.R.S.), Paris (FR); INSTITUT NATIONAL DE LA SANTE ET DE LA RECHERCHE MEDICALE (INSERM), Paris (FR); ECOLE SUPRERIEURE DE PHYSIQUE ET DE CHIMIE INDUSTRIELLES DE LA VILLE DE PARIS, Paris (FR); UNIVERSITÉ PARIS DIDEROT—PARIS 7, Paris (FR)

( * ) Notice: Subject to any disclaimer, the term of this patent is extended or adjusted under 35 U.S.C. 154(b) by 343 days.

(21) Appl. No.: 15/115,168

(22) PCT Filed: Jan. 12, 2015

(86) PCT No.: PCT/FR2015/050058
§ 371 (c)(1),
(2) Date: Jul. 28, 2016

(87) PCT Pub. No.: WO2015/114232
PCT Pub. Date: Aug. 6, 2015

(65) Prior Publication Data
US 2016/0345938 A1    Dec. 1, 2016

(30) Foreign Application Priority Data
Jan. 31, 2014  (FR) ..................... 14 00265

(51) Int. Cl.
*A61B 8/08* (2006.01)
*A61B 8/00* (2006.01)

(52) U.S. Cl.
CPC ............ *A61B 8/485* (2013.01); *A61B 8/085* (2013.01); *A61B 8/0858* (2013.01);
(Continued)

(58) Field of Classification Search
CPC ....... A61B 8/485; A61B 8/085; A61B 8/0858; A61B 8/0883; A61B 8/4483; A61B 8/5223; A61B 8/4281
See application file for complete search history.

(56) References Cited

U.S. PATENT DOCUMENTS

| | | |
|---|---|---|
| 6,770,033 B1 | 8/2004 | Fink et al. |
| 7,252,004 B2 | 8/2007 | Fink et al. |

(Continued)

OTHER PUBLICATIONS

Wang et al., "Imaging Transverse Isotropic Properties of Muscle by Monitoring Acoustic Radiation Force Induced Shear Waves Using a 2-D Matrix Ultrasound Array." IEEE Transactions on Medical Imaging, 2013. 32(9). p. 1671-1684.*

(Continued)

*Primary Examiner* — Catherine B Kuhlman
*Assistant Examiner* — Sean A Frith
(74) *Attorney, Agent, or Firm* — B. Aaron Schulman, Esq.; Stites & Harbison, PLLC

(57) ABSTRACT

A method for characterizing an anisotropic soft medium (C) including fibers and having an outer surface (1), by observing in different propagation directions, the propagation of a divergent shear wave from a central area (10) in the anisotropic soft medium. A propagation parameter of the shear wave is inferred therefrom in each of the propagation directions, and then a direction of the fibers of the anisotropic soft medium, a rheological elasticity parameter are determined in a direction perpendicular to the fibers and a rheological elasticity parameter in the direction of the fibers.

24 Claims, 2 Drawing Sheets

(52) U.S. Cl.
CPC .......... *A61B 8/0883* (2013.01); *A61B 8/4483* (2013.01); *A61B 8/5223* (2013.01); *A61B 8/4281* (2013.01)

(56) References Cited

U.S. PATENT DOCUMENTS

| | | | |
|---|---|---|---|
| 7,553,283 B2 | 6/2009 | Sandrin et al. | |
| 8,734,352 B2 | 5/2014 | Burcher et al. | |
| 9,339,256 B2 | 5/2016 | Specht et al. | |
| 2005/0251042 A1 | 11/2005 | Sandrin et al. | |
| 2010/0228126 A1* | 9/2010 | Emery | A61B 8/14 600/439 |
| 2011/0028838 A1* | 2/2011 | Pernot | A61B 5/0048 600/437 |
| 2012/0116220 A1 | 5/2012 | Burcher et al. | |
| 2013/0051178 A1* | 2/2013 | Rybyanets | A61B 8/00 367/138 |
| 2013/0131511 A1* | 5/2013 | Peterson | A61B 5/0048 600/438 |
| 2013/0211254 A1* | 8/2013 | Aase | A61B 8/0883 600/438 |
| 2013/0218012 A1* | 8/2013 | Specht | A61B 8/485 600/438 |
| 2013/0317361 A1* | 11/2013 | Tabaru | G01S 7/52042 600/438 |
| 2014/0364734 A1* | 12/2014 | Huang | A61B 5/7275 600/447 |
| 2015/0099971 A1 | 4/2015 | Sandrin et al. | |
| 2015/0192547 A1* | 7/2015 | Lee | A61B 8/485 73/641 |
| 2016/0256134 A1 | 9/2016 | Specht et al. | |

OTHER PUBLICATIONS

Hsu et al., "Shear Wave Anisotropy Imaging." IEEE Ultrasonics Symposium, 2003. p. 1090-1093.*
International Search Report for PCT/FR2015/050058 dated May 24, 2015.
Wei-Ning, et al., "Mapping Myocardial Fiber Orientation Using Echocardiography-Based Shear Wave Imaging", May 2, 2012, pp. 554-562, vol. 31, No. 3, IEEE Transactions on Medical Imaging, IEEE Service Center, Piscataway, NY.
Brum, et al., "In vivo evaluation of the elastic anisotropy of the human Achilles tendon using shear wave dispersion analysis", Jan. 17, 2014, pp. 505-523, vol. 59, Phys. Med. Biol.
Mace, et al., "In Vivo Mapping of Brain Elasticity in Small Animals Using Shear Wave Imaging", Mar. 2, 2011, pp. 550-558, vol. 30, No. 3, IEEE Transactions on Medical Imaging, IEEE Service Center.
Lee, et al., "Ultrasound Elastic Tensor Tensor Imaging: Comparison with MR Diffusion Tensor Imaging in the Myocardium," 2012, pp. 5075-5095, vol. 57, Physics in Medicine and Biology.

* cited by examiner

ULTRASONIC METHOD AND DEVICE FOR CHARACTERISING WEAK ANISOTROPIC MEDIA, AND ULTRASONIC PROBE ASSEMBLY FOR SUCH A CHARACTERISATION DEVICE

FIELD OF THE INVENTION

The invention relates to methods and devices for characterization of anisotropic soft media; and to the sets of ultrasound probes for such characterization devices.

BACKGROUND OF THE INVENTION

Characterization of anisotropic soft media including fibers, such as skeletal muscles or the myocardium has already been proposed by imaging of the propagation of shear waves in these media. More particularly, measuring the value of the shear modulus of these media along the fibers and perpendicularly to the fibers has been proposed, by successively having shear waves propagate in the medium and by imaging their propagation every time in a different direction, by means of an ultrasonic transducer array which is rotated by a few degrees between two shear wave emissions (W.-N. Lee, M. Pernot, M. Couade, E. Messas, P. Bruneval, A. Bel, A. A. Hagège, M. Fink, and M. Tanter, "Mapping Myocardial Fiber Orientation Using Echocardiography-Based Shear Wave Imaging," IEEE Trans. Med. Imaging, Vol. 31, pp. 554-562, 2012). The propagation velocity of the shear waves is thus determined in each direction. By breaking down the velocity measurements into singular values, it is possible to obtain both the direction of the fibers and the shear moduli along the fibers and perpendicularly to the fibers, as taught by Lee et al. (W.-N. Lee, B. Larrat, M. Pernot, and M. Tanter, "Ultrasound Elastic Tensor Imaging: Comparison with MR Diffusion Tensor Imaging in the Myocardium," Physics in Medicine and Biology, Vol. 57, pp. 5075-5095, 2012).

These known methods however have the drawback of being relatively slow to apply. Consequently, they notably do not allow characterization of mobile fiber media such as the myocardium of a patient or a skeletal muscle of a patient.

OBJECTS AND SUMMARY OF THE INVENTION

The present invention notably has the purpose of overcoming these drawbacks.

For this purpose, the invention proposes a method for characterizing an anisotropic soft medium comprising at least one portion including fibers and having an outer surface, this method comprising the following steps:

(a) a measurement step during which at least one shear wave is generated, which propagates as a divergent wave from a central area in the anisotropic soft medium and a propagation of said at least one shear wave is observed in several predetermined propagation directions from said central area, with ultrasonic observation transducers from the surface of the anisotropic soft medium, by maintaining fixed the ultrasonic observation transducers, said predetermined propagation directions comprising at least two directions forming between them an angle different from 0 degrees and different from 180 degrees, said ultrasonic observation transducers being positioned at least along said predetermined propagation directions and said measurement step being carried out within a period of less than 50 ms;

(b) at least one computing step during which at least one propagation parameter of the shear wave is determined in each of said predetermined propagation directions from data collected during the measurement step (a);

(c) a characterization step during which, from said at least one determined propagation parameter of the shear wave in each of the propagation directions in the computing step (b), at least one rheological characteristic of the anisotropic soft medium is determined, selected from a direction of the fibers of the anisotropic soft medium, a rheological elasticity parameter in a direction perpendicular to the fibers and a rheological elasticity parameter in the direction of the fibers is determined.

By means of these arrangements, it is possible to instantaneously access the direction of the fibers and/or the elasticity parameters, without having to rotate the measurement probe and therefore it is possible to easily carry out measurements in vivo.

In various embodiments of the method according to the invention, it is optionally possible to further resort to either one of the following arrangements:

the rheological elasticity parameters determined during the characterization step (c) are elasticity moduli;

during the measurement step (a), the shear wave is generated over a certain range of depths in the anisotropic soft medium and the propagation of said at least one shear wave is observed at different depths inside said range of depths, during the computing step (b), said at least one propagation parameter of the shear wave is determined in each of said predetermined propagation directions (P) predetermined at said different depths, and during the characterization step (c), said at least one rheological characteristic is determined at said different depths;

during the measurement step (a), the predetermined propagation directions in which the propagation of the shear wave is observed, are of a number comprised between 3 and 20, advantageously between 5 and 10;

during the measurement step (a), the propagation of said at least one shear wave is observed simultaneously in all of said predetermined propagation directions, with all the ultrasonic observation transducers at the same time;

during the measurement step (a), several shear waves are successively emitted and the propagation of each shear wave is successively observed in at least one of said predetermined propagation directions, with a portion of the ultrasonic observation transducers;

during the measurement step (a), the passage of the shear wave in predetermined measurement points respectively positioned along said predetermined propagation directions is detected, and during the computing step (b), the propagation parameter of the determined shear wave is a representative parameter either of a propagation velocity of the shear wave, or a flight time of the shear wave from the central area;

the shear wave is generated from a central axis perpendicular to the surface of the anisotropic soft medium and said measurement points where the passage of the shear wave is detected, are each located at a distance from the central axis of less than 2 cm, advantageously less than 0.5 cm;

during the measurement step (a), the passage of the shear wave is detected by emission of acoustic compressional waves in said predetermined measurement points by said ultrasonic observation transducers, at a rate of at least 300 shots of ultrasonic compressional waves per second, ultrasonic signals reflected by the anisotropic soft medium are sensed by said ultrasonic observation transducers, and internal displacements are thereby determined (absolute displacements or deformations or displacement or deformation velocities) of said anisotropic soft medium upon passage of the shear wave at said predetermined measurement points;

during the measurement step (a), a single ultrasonic observation transducer is used per measurement point;

during the measurement step (a), the shear wave is generated by having an ultrasonic excitation transducer which bears said ultrasonic observation transducers, emits an excitation ultrasonic wave focused on the central area, which displaces the anisotropic soft medium along said central axis;

during the characterization step (c), said at least one rheological characteristic is determined, determining a corresponding elastic tensor corresponding to the singular values, the values of the propagation parameter in the different predetermined propagation directions, and then by breaking down this elastic tensor into singular values;

during the measurement step (a), the shear wave is generated from a central axis and during the characterization step (c), a substantially ellipsoidal curve $C(V(\Theta) \cdot \cos \Theta, V(\Theta) \cdot \sin \Theta)$, wherein $V(\Theta)$ is the value of the propagation parameter in a plane perpendicular to said central axis and $\Theta$ is an angle designating the propagation direction in said plane relatively to a reference system belonging to said plane is determined by interpolation according to propagation parameters values computed at the computing step (b) in said predetermined propagation directions, depending on the values of the propagation parameter computed in the computing step (b) in said predetermined propagation directions; the direction of the fibers corresponding to an angle $\Theta_0$ corresponding to the maximum of $V(\Theta)$, the rheological elasticity parameter in the direction of the fibers being determined according to $V(\Theta_0)$ and the rheological elasticity parameter in the direction perpendicular to the fibers being determined according to $V(\Theta_0 + \pi/2)$;

the anisotropic soft medium comprises at least one portion of an operating human or animal muscle and the method includes several measurement steps (a), computing steps (b) and characterization steps (c), a physiological parameter related to the contraction of the muscle is inferred therefrom.

Moreover, the object of the invention is also a device for characterizing an anisotropic soft medium having at least one portion comprising fibers and having an outer surface, this characterization device comprises an electronic control device which controls an excitation probe and ultrasonic observation transducers, the excitation probe being adapted for generating a shear wave in the anisotropic soft medium from a central area and the ultrasonic observation transducers being positioned along several predetermined propagation directions from said central area, said predetermined propagation directions comprising at least two directions forming between them an angle different from 0 degrees and different from 180 degrees, the electronic control device being adapted for, when the excitation probe and the ultrasonic observation transducers are positioned at the surface of the anisotropic soft medium:

(a) generating by the excitation probe of at least one shear wave suitable for propagating divergently from the central area into the anisotropic soft medium and having the ultrasonic observation transducers observe, within a total observation period of less than 50 ms, a propagation of the shear wave in said predetermined propagation directions from said central area;

(b) determining, from data collected by the ultrasonic observation transducers, at least one propagation parameter of the shear wave simultaneously in each of said predetermined propagation directions;

(c) determining, from said at least one propagation parameter of the shear wave in each of the predetermined propagation directions, at least one rheological characteristic of the anisotropic soft medium, selected from a direction of the fibers of the anisotropic soft medium, a rheological elasticity parameter in a direction perpendicular to the fibers and a rheological elasticity parameter in the direction of the fibers.

In diverse embodiments of the characterization device according to the invention, it is optionally possible to further resort to either one of the following arrangements:

said ultrasonic observation transducers being in a number comprised between 3 and 20, advantageously between 5 and 10;

the electronic control device is adapted for detecting the passing of the shear wave facing each ultrasonic observation transducer and the propagation parameter of the shear wave, determined by the central unit, is a representative parameter either of a propagation velocity of the shear wave, or of a time of flight of the shear wave;

the electronic control device is suitable for detecting the passing of the shear wave:

by having the ultrasonic observation transducers emit acoustic compressional waves at a rate of at least 300 shots of ultrasonic compressional waves per second, by having ultrasonic signals reflected by the anisotropic soft medium being sensed by the ultrasonic observation transducers, and by thereby determining internal displacements of said anisotropic soft medium upon passing of the shear wave facing said ultrasonic observation transducers;

the excitation probe is an ultrasonic transducer substantially disk-shaped which bears the ultrasonic observation transducers.

Finally, the object of the invention is further a set of ultrasonic probes for a device as defined above, including an ultrasonic excitation transducer substantially disk-shaped and adapted for emitting an ultrasonic compressional wave along a central axis in order to displace the anisotropic soft medium along said central axis by radiation pressure and thus have a divergent shear wave propagate in the medium from said central axis, said ultrasonic excitation transducer bearing ultrasonic observation transducers respectively distributed in different divergent propagation directions with respect to said central axis and positioned at a distance of less than e cm from said central axis, said propagation directions comprising at least two directions forming between them an angle different from 0 degrees and different from 180 degrees. Advantageously, the ultrasonic observation transducers are equidistributed on a circle centered on the central axis, each ultrasonic observation transducer being adapted for emitting compressional waves as a beam parallel to the central axis.

SHORT DESCRIPTION OF THE DRAWINGS

Other features and advantages of the invention will become apparent during the following description of one of its embodiments, given as a non-limiting example, with reference to the appended drawings.

In the drawings.

MORE DETAILED DESCRIPTION

In the different figures, the same references designate identical or similar elements.

Figure 1:
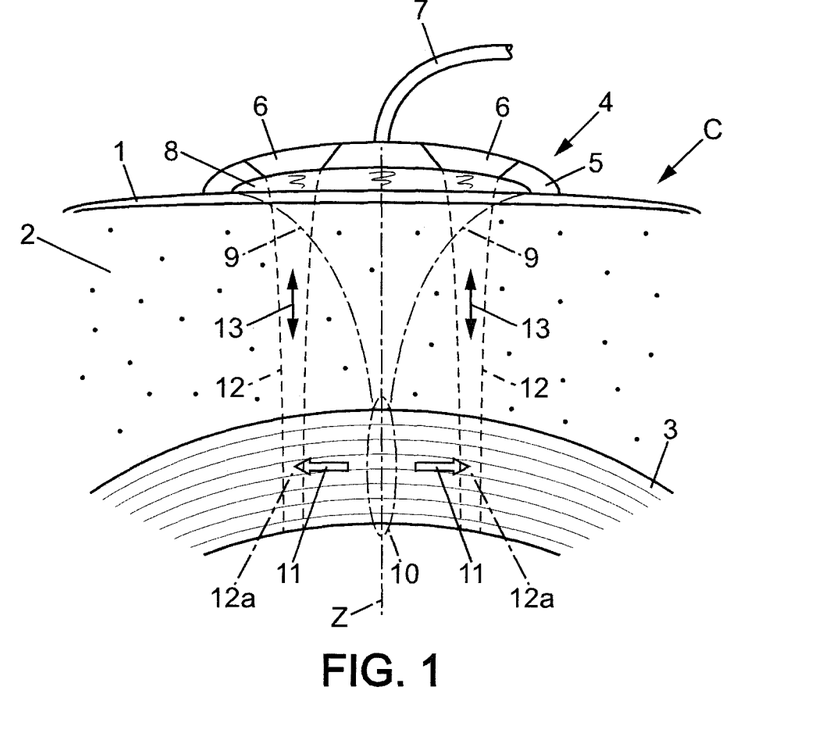
FIG. 1 is a sectional view illustrating the application of a characterization method according to an embodiment of the invention.
Figure 2:
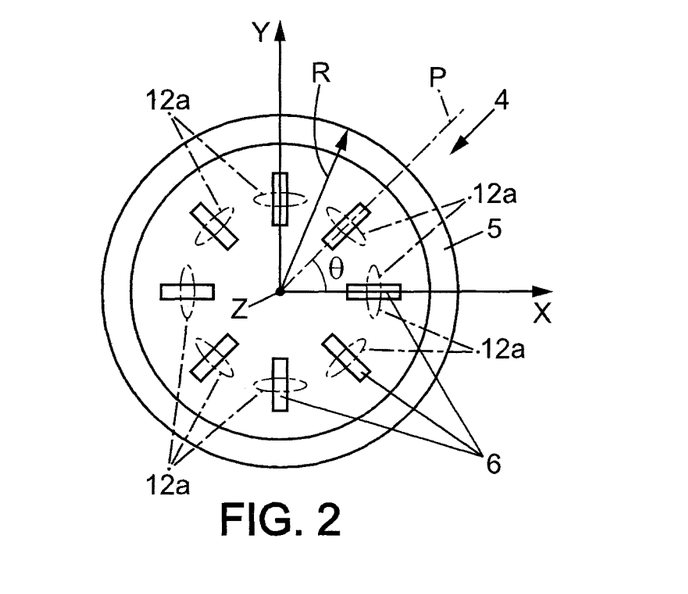
FIG. 2 is a planar view of a set of ultrasonic probes visible in FIG. 1.

As schematically illustrated in FIGS. 1 and 2, the object of the invention is to characterize an anisotropic soft medium such as a portion of a human or animal body C, notably a living body, comprising at least one portion 3 including fibers and having an outer surface 1. For example, the outer surface may be the skin of the human being or animal, and the portion 3 may be a portion of the heart, notably the myocardium, or further a skeletal muscle. The portion 3 may optionally be separated from the outer surface 1 by non-fiber tissues 2.

This characterization is carried out by means of a probe set 4 including an excitation probe 5 and observation probes 6.

The excitation probe 5 may notably be an ultrasonic excitation transducer substantially disc or cup-shaped having a central axis Z positioned in the direction of the depth of the anisotropic soft medium C when the excitation probe is being used. This excitation probe 5 optionally includes a concave face intended to be applied against the outer surface 1, generally with filling of the concavity of this face with a gel 8 conventionally used in echography. The excitation probe 5 is adapted for emitting an ultrasonic compressional wave 9 in the anisotropic soft medium C along said central axis Z, the focal spot of which is in a central area 10 extending over a few centimeters along the central axis Z (for example 1 to 6 cm) and having a width of a few millimeters perpendicularly to the central axis Z (for example from 0.2 to 3 mm).

The position and the length of the focal spot 10 along the central axis Z are designed so that statistically, when the excitation probe is positioned against the outer surface 1, the focal spot is normally found at least partly in the fiber portion 3 to be characterized for the examined human beings or animals. Thus, for characterization of the myocardium in a human being, the focal spot 10 for example begins at a depth z from 2 to 4 cm and for example ends at a depth z from 5 to 10 cm.

The excitation probe 5 may for example have a radius R of less than 3 cm, advantageously less than 2 cm.

The observation probes 6 may be in a number greater than or equal to 2, advantageously greater than or equal to 3, for example comprised between 3 and 20, advantageously between 5 and 10. These observation probes are 8 in number in the illustrated example.

The observation probes 6 are distributed around the central axis Z, respectively matching different propagation directions P divergent relatively to said central axis Z. In every case, the propagation directions P comprise at least two propagation directions which form between them an angle different from 0 degrees and different from 180 degrees.

The observation probes (6) may be positioned at a distance of less than 2 cm from said central axis Z, for example less than 0.5 cm. The observation probes 6 may be advantageously equi-distributed on a circle centered on the central axis Z. In the following, the divergent propagation directions P will be localized in an orthonormal reference system X, Y in a plane perpendicular to the central axis Z, by their angle Θ with respect to the X axis.

The observation probes 6 may each be an ultrasonic observation transducer or optionally a group of ultrasonic observation transducers, of the type conventionally used in medical imaging, focused at a relatively large distance parallel to the central axis Z so as to each emit an ultrasonic compressional wave forming a beam 12 parallel to the axis Z as notably indicated by the arrows 13 on FIG. 1.

Advantageously, each observation probe 6 is formed by a single ultrasonic observation transducer. The ultrasonic observation transducers 6 may be conformed as arrays extending radially with respect to the Z axis and having some concavity towards the medium C, so that the focal spot 12a of each ultrasonic observation transducer 6 is located at about the same depth as the focal spot 10 in the medium C, and so that this focal spot 12a has a small dimension in the radial direction with respect to the Z axis, for example of the order of 0.1 to 2 mm and a larger dimension, of the order of a few millimeters in the orthoradial direction. The focal spots 12a corresponding to the different ultrasonic observation transducers are preferably separated from each other.

Advantageously, the observation probes 6 are borne by the excitation probe 5, and for example may be included in recesses made in the thickness of the excitation probe 5.

Figure 3:
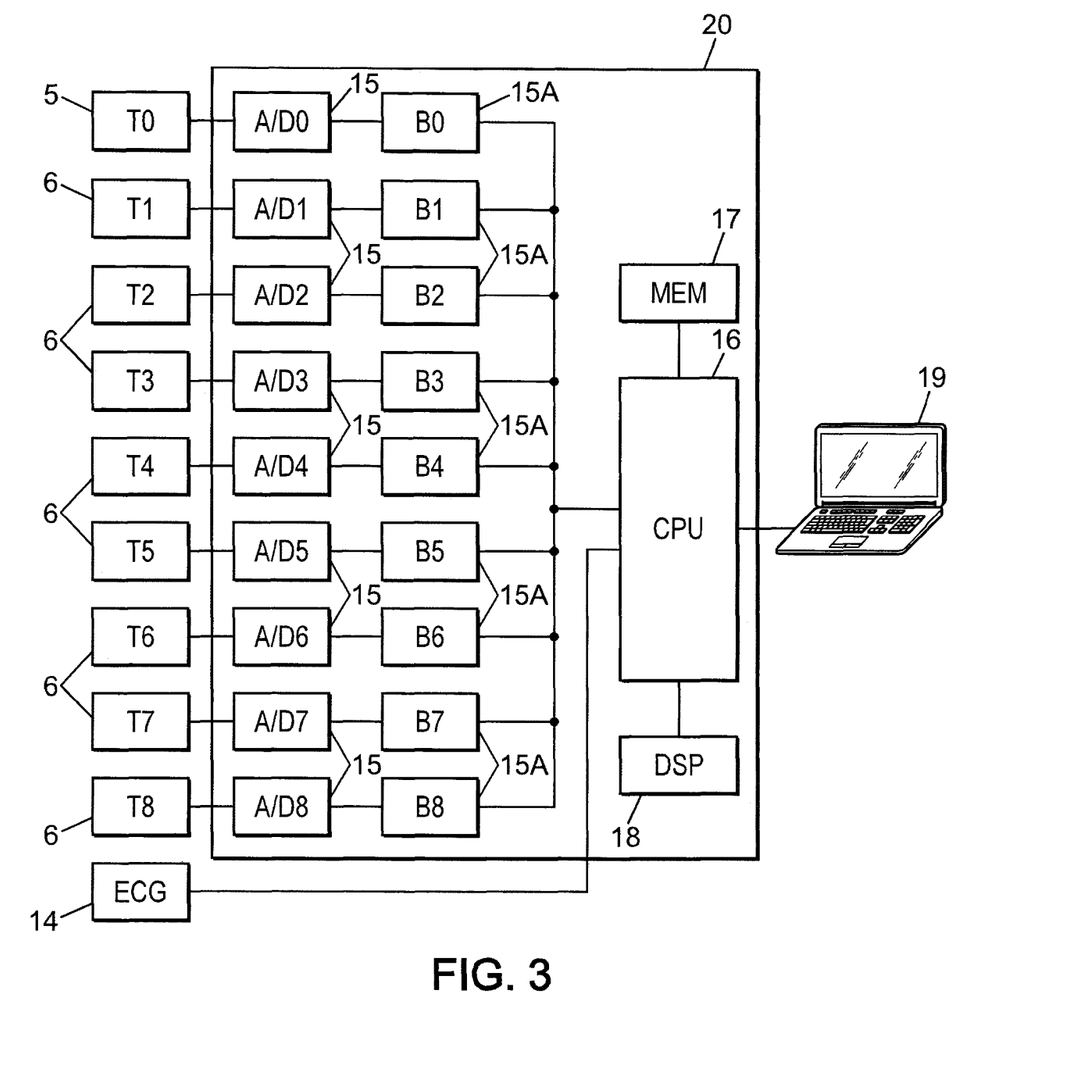
FIG. 3 is a schematic view of a characterization device to which belongs the set of ultrasonic probes of FIG. 2.

The excitation probe 5 and the observation probes 6 communicate with a control device, for example via a multi-wire cable 7. As illustrated in FIG. 3, this control device may comprise a computer 19 or the like communicating with a specific electronic casing 20, itself connected to the set of probes 4 through the cable 7. It will be noted that the control device may optionally be a single apparatus integrating all the functionalities of the electronic casing 20 and of the computer 19.

In the illustrated example, the electronic casing 20 may include as many channels as there are transducers, for example 9 channels, respectively connected to the excitation probe 5 (T0) and to the observation probes 6 (T1-T8). Each of these channels may include an analogue-digital converter 15 (A/D0-AD8) associated with a buffer memory 15A (B0-B8) and communicating with an electronic central unit 16 (CPU) such as a microprocessor or the like, which itself may communicate for example with a memory 17 (MEM) and a signal processing circuit 18 (DSP), as well as with the computer 19. The electronic central unit 16 may optionally further communicate with an electrocardiogram apparatus 14 (ECG).

The device which has just been described operates as follows.

(a) Measurement Step

When a user intends to characterize the fiber portion 3 of the medium C, he/she applies the probe set 4 on the skin 1 as explained earlier and initiates a measurement step (a) during which the electronic central unit 16 will first have an ultrasonic wave emitted focussed by the excitation probe 5 for a short period, in order to generate a displacement of the tissues along the axis Z by the effect of wave pressure, for example on the general principle explained in document WO2004/021038.

This shear wave 11 substantially propagates radially with respect to the Z axis (see FIG. 1) and during this propagation, the electronic central unit 16 has the medium C simultaneously observed by all the observation probes 6, in order to observe the propagation of the shear wave 11. For this purpose, the electronic central unit 16 has all the observation probes 6 emit simultaneously, at a fast rate (for example 300 shots per second or more), ultrasonic compressional waves and said observation probe 6 sense the ultrasonic signals reflected by the tissues 3, as notably explained in documents WO00/55616 and WO2004/021038, and these signals are stored in memory first in buffer memories 15a and then in the memory 17.

This measurement step for example lasts for a few milliseconds.

Optionally, the electronic casing 20 might include as many channels as there are transducers. For example, the electronic casing 20 may include a channel A/D0-B0 for the ultrasonic excitation transducer 5 and a channel A/D1-B1 successively connected to the various ultrasonic observation transducers 6 through a switching device (not shown). In this case, the measurement step (a) includes several successive emissions of a shear wave each followed by the observation of its propagation through one of the observation probes 6, the process being repeated for each observation probe 6. Even in this case, the measurement step is very short, less than 50 ms.

(b) Computing Step

In a subsequent computing step (b), carried out in real time or offline, the reflected signals stored in memory are utilized by the electronic central unit 16 or the computer 19. During this processing, said signals are used for determining internal displacements or deformations of the tissues 3 over time facing each observation probe 6, for example by correlation computations on the sensed signals, as notably explained in documents WO00/55616 and WO2004/021038.

Thus it is therefore possible to localize the passing of the elastic shear wave in front of each observation probe 6, and this at each depth in the tissues 3. For example, the passing of the shear wave may thus be localized at a predetermined number of depths in the tissues 3, for example between 10 and 30 depths, for example millimeter by millimeter.

The electronic central unit 16 or the computer 19 then determines at each depth, the time of flight t of the shear wave between the excitation probe 5 and each observation probe 6, or another parameter representative of the time of flight, or further another propagation datum representative of the propagation of the shear wave, and the propagation velocity V of the shear wave is inferred therefrom at the relevant depth in the radial direction P corresponding to each observation probe 6.

(c) Characterization Step

It is then possible to determine at least one rheological characteristic of the medium 3, selected from among direction of the fibers, a rheological elasticity parameter (notably an elasticity modulus) in a direction perpendicular to the fibers and a rheological elasticity parameter (notably an elasticity modulus) in the direction of the fibers. Advantageously, these rheological characteristics are determined at the same time.

Said rheological characteristics may be determined by diverse methods, for example by interpolation or more preferentially by breaking down into singular values.

1. Interpolation

In this method, depending on the computed values of the propagation velocity in the computing step (b) in each of the propagation directions P, a substantially ellipsoidal curve $C(V(\Theta) \cdot \cos \Theta, V(\Theta) \cdot \sin \Theta)$ wherein $V(\Theta)$ is the value of the propagation parameter in the plane X, Y is determined by interpolation. The direction of the fibers corresponds to an angle $\Theta_0$ corresponding to the maximum of $V(\Theta)$, the rheological elasticity parameter in the direction of the fibers is then determined according to $V(\Theta_0)$ and the rheological elasticity parameter in the direction perpendicular to the fibers being determined according to $V(\Theta_0+\pi/2)$. For example, when these parameters are elasticity moduli Epar parallel to the fibers and Eperp perpendicularly to the fibers, these elasticity moduli may be determined by the formulae, formula $$V(\theta 0) = \sqrt{\frac{Epar}{3\rho}} \text{ and } V(\theta 0 + \pi/2) = \sqrt{\frac{Eperp}{3\rho}},$$

wherein $\rho$ is the density of the medium 3.

2. Breaking it Down into Singular Values

In this method, at each depth, the elastic propagation tensor of the ultrasonic wave in the medium 3 is determined first at each depth, from the measured propagation velocities.

This tensor is a matrix M here of rank 2 since the propagation is only accomplished in the plane X, Y:

$$M = \begin{bmatrix} E_{XX}, & E_{XY} \\ E_{XY}, & E_{YY} \end{bmatrix},$$

wherein the components E are elastic moduli. This elastic tensor is notably defined by Royer and Dieulesaint (2000; *Elastic Waves in Solids I: Free and Guided Propagation*: Springer-Verlag Berlin Heidelberg).

As explained in the article of Lee et al. mentioned above (W.-N. Lee, B. Larrat, M. Pernot, and M. Tanter, "Ultrasound Elastic Tensor Imaging: Comparison with MR Diffusion Tensor Imaging in the Myocardium," Physics in Medicine and Biology, Vol. 57, pp. 5075-5095, 2012), the tensor M may be determined from the velocities $V(\Theta)$ determined in the computing step (b), by solving the equation:

$$\begin{bmatrix} \rho V(\theta_1)^2 \\ \vdots \\ \rho V(\theta_N)^2 \end{bmatrix} = \begin{bmatrix} \cos^2\theta_1 & 2\cos\theta_1\sin\theta_1 & \sin^2\theta_1 \\ & \vdots & \\ \cos^2\theta_N & 2\cos\theta_N\sin\theta_N & \sin^2\theta_N \end{bmatrix} \begin{bmatrix} E_{XX} \\ E_{XY} \\ \mu_{YY} \end{bmatrix} \quad (1)$$

wherein $\rho$ is the density of the medium 3, N is the number of transducers and $\Theta 1 \ldots \Theta N$ are the angles of the different propagation directions P corresponding to the observation probes 6.

Always as explained by the aforementioned article Lee et al., the tensor M may then be broken down into singular values in order to obtain a diagonal matrix M0 giving the aforementioned parameters Epar, Eperp:

$$M0 = \begin{bmatrix} E_{PAR} & 0 \\ 0 & E_{PERP} \end{bmatrix}.$$

This determination is accompanied by the determination of the direction $\Theta 0$ of the fibers at the relevant depth, since one has the relationship:

$M = R \cdot M0 \cdot R^T$, wherein R is the rotation matrix corresponding to the angle $\Theta 0$:

$$R = \begin{bmatrix} \cos\theta_0 & -\sin\theta_0 \\ \sin\theta_0 & \cos\theta_0 \end{bmatrix}.$$

The measurement steps (a), the computing steps (b) and the characterization steps (c) may be repeated at a relatively fast rate, so as to follow the heart or another muscle in its operation and to give successive values of the rheological characteristics, parameters of the medium 3 for example over a full operating cycle of the muscle forming the medium 3. When this is the heart, the successive measurements may be synchronized with the heartbeat cycle by means of the data communicated by the electrocardiograph 14 to the electronic central unit 16. A value of a physiological parameter related to the contraction of the muscle, for example the contractility, maximum hardness or other parameter is inferred therefrom.

It will be noted that the signals sensed by the observation probes may also give the possibility of readjusting the successive measurements relatively to each other by localizing the deformations or displacements of the medium 3 due to the operation of the muscle forming this medium 3.

The invention claimed is:

1. A method for determining at least one rheological characteristic of an anisotropic soft medium comprising at least one portion comprising fibers and having a central area and an outer surface, said method comprising:
    (a) obtaining a measurement by generating at least one shear wave which propagates by diverging from the central area in the anisotropic soft medium, wherein propagation of said at least one shear wave is observed in at least two predetermined propagation directions with ultrasonic observation transducers, from the outer surface of the anisotropic soft medium, said ultrasonic observation in at least two predetermined propagation directions from said central area occurring by maintaining the ultrasonic observation transducers in a fixed position in relation to the anisotropic soft medium, said predetermined propagation directions comprising at least two directions forming between them an angle different from 0 degrees and different from 180 degrees, said ultrasonic observation transducers being positioned along said at least two predetermined propagation directions so that a complete measurement of said anisotropic soft material is obtained within a period of less than 50 ms,
    wherein the at least one shear wave is generated from a central axis perpendicular to the outer surface of the anisotropic soft medium and measurement points where passing of the at least one shear wave is detected, are each located at a distance from said central axis of less than 2 cm,
    wherein the at least one shear wave is generated by having an ultrasonic excitation transducer bearing said ultrasonic observation transducers emit an ultrasonic excitation wave focused on the central area, which displaces the anisotropic soft medium along said central axis,
    wherein the at least one shear wave is generated over a certain range of depths in the anisotropic soft medium and the propagation of said at least one shear wave is observed at different depths inside said range of depths,
    wherein said ultrasonic observation transducers are equidistributed on a circle centered on the central axis, and wherein the propagation of said at least one shear wave is simultaneously observed in all of said predetermined propagation directions, with all the ultrasonic observation transducers;
    (b) determining at least one propagation parameter of the at least one shear wave from data collected during said measurement in each of said predetermined propagation directions,
    wherein said at least one propagation parameter of the at least one shear wave is determined in each of said predetermined propagation directions at said different depths; and
    (c) characterizing at least one propagation parameter of the shear wave, determined in each of said predetermined propagation directions,
    wherein said at least one rheological characteristic is selected from the group consisting of a direction of the fibers of the anisotropic soft medium, a rheological elasticity parameter in a direction perpendicular to the fibers, and a rheological elasticity parameter in the direction of the fibers, and
    wherein said at least one rheological characteristic is determined at said different depths.

2. The method according to claim 1, wherein the rheological elasticity parameters determined during (c) are elasticity moduli.

3. The method according to claim 1, wherein during (a), the predetermined propagation directions in which the propagation of the at least one shear wave is observed, are in a number between 3 and 20.

4. The method according to claim 1, wherein:
    during (a), the passing of the at least one shear wave in predetermined measurement points respectively positioned along said predetermined propagation directions is detected,
    and during (b), the determined propagation parameter of the at least one shear wave is a representative parameter of either a propagation velocity of the at least one shear wave, or a time of flight of the at least one shear wave from the central area.

5. The method according to claim 4, wherein the at least one shear wave is generated from a central axis perpendicular to the outer surface of the anisotropic soft medium and said measurement points where the passing of the at least one shear wave is detected, are each located at a distance from said central axis of less than 2 cm.

6. The method according to claim 4, wherein during (a):
    the passing of the at least one shear wave is detected by emission of acoustic compressional waves in said predetermined measurement points by said ultrasonic observation transducers, at a rate of at least 300 shots of ultrasonic compressional waves per second,
    ultrasonic signals reflected by the anisotropic soft medium are sensed by said ultrasonic observation transducers, and
    internal displacements of said anisotropic soft medium are thereby determined upon passing of the at least one shear wave at said predetermined measurement points.

7. The method according to claim 4, wherein during (a), a single ultrasonic observation transducer is used per measurement point.

8. The method according to claim 1, wherein during (a), the at least one shear wave is generated by having an ultrasonic excitation transducer which bears said ultrasonic observation transducers, emits an ultrasonic excitation wave focused on the central area, which displaces the anisotropic soft medium along said central axis.

9. The method according to claim 1, wherein during (c), said at least one rheological characteristic determining an elastic tensor corresponding to the singular values the propagation parameter values in the different predetermined propagation directions, and then by breaking down this elastic tensor into singular values, is determined.

10. The method according to claim 1, wherein during (a), the at least one shear wave is generated from a central axis, and during (c), an ellipsoidal curve $C(V(\Theta) \cdot \cos \Theta, V(\Theta) \cdot \sin \Theta)$ is determined by interpolation according to propagation parameters values computed at (b) in said predetermined propagation directions, wherein $V(\Theta)$ is a value of the propagation parameter in a plane perpendicular to said central axis and $\Theta$ is an angle designating a propagation direction in said plane with respect to a reference system belonging to said plane, the direction of the fibers corresponding to an angle $\Theta_0$ corresponding to a maximum of $V(\Theta)$, the rheological elasticity parameter in the direction of the fibers being determined according to $V(\Theta_0)$ and the rheological elasticity parameter in the direction perpendicular to the fibers being determined according to $V(\Theta_0+\pi/2)$.

11. The method according to claim 1, wherein the anisotropic soft medium comprises at least one portion of an operating human or animal muscle and the method includes several successive conductings of (a), (b), and (c), and further comprises inferring a physiological parameter related to a contraction of the muscle based on the results of the several successive conductings of (a), (b), and (c).

12. The method for characterizing an anisotropic soft medium according to claim 1 wherein propagation of said at least one shear wave is observed in at least two predetermined propagation directions with ultrasonic observation transducers that each emit simultaneously or successively ultrasonic compressional waves and sense ultrasound reflected by the anisotropic soft medium.

13. A measuring device for determining at least one rheological characteristic of an anisotropic soft medium comprising at least one portion comprising fibers and having a central area and an outer surface, and an electronic control device which controls an excitation probe and ultrasonic observation transducers, the excitation probe being adapted for generating at least one shear wave in the central area and the ultrasonic observation transducers being positioned along several predetermined propagation directions from said central area, said predetermined propagation directions comprising at least two directions forming between them an angle different from 0 degrees and different from 180 degrees, the electronic control device being adapted for controlling the elements of the measuring device for carrying out the method of claim 1 wherein during (a), the propagation of said at least one shear wave is simultaneously observed in all of said predetermined propagation directions, with all of said ultrasonic observation transducers.

14. The device according to claim 13, wherein a number of said ultrasonic observation transducers is between 3 and 20.

15. The device according to claim 14, wherein the electronic control device is adapted for detecting passing of the at least one shear wave facing each ultrasonic observation transducer and the propagation parameter of the at least one shear wave, determined by the central unit, is a representative parameter of either a propagation velocity of the at least one shear wave, or of a time of flight of the at least one shear wave.

16. The device according to claim 15, wherein the electronic control device is adapted for detecting the passing of the at least one shear wave:

by having the ultrasonic observation transducers emit acoustic compressional waves at a rate of at least 300 shots of ultrasonic compressional waves per second, by having ultrasonic signals reflected by the anisotropic soft medium sensed by the ultrasonic observation transducers, and by thereby determining internal displacements of said anisotropic soft medium upon passing of the at least one shear wave facing said ultrasonic observation transducers.

17. The device according to claim 16, wherein the excitation probe is an ultrasonic disk-shaped transducer which bears the ultrasonic observation transducers.

18. An ultrasonic probe set comprising the measuring device according to claim 13, and further comprising a disk-shaped ultrasonic excitation transducer adapted for emitting an ultrasonic compressional wave along a central axis in order to displace the anisotropic soft medium along said central axis by pressure of radiation and thus causing propagation in the medium of a divergent at least one shear wave from said central axis, said ultrasonic excitation transducer bearing ultrasonic observation transducers respectively distributed in different divergent propagation directions with respect to said central axis and positioned at a distance of less than 2 cm from said central axis, each ultrasonic observation transducer being adapted for emitting compressional waves as a beam parallel to the central axis, said propagation directions comprising at least two directions forming between them an angle different from 0 degrees and different from 180 degrees.

19. A method for characterizing an anisotropic soft medium comprising at least one portion including fibers and having a central area and an outer surface, said method comprising:

(a) obtaining a measurement by generating at least one shear wave which propagates by diverging from the central area, wherein propagation of said at least one shear wave is observed with ultrasonic observation transducers, from the outer surface of the anisotropic soft medium, in at least two predetermined propagation directions from said central area by maintaining fixed the ultrasonic observation transducers in relation to the anisotropic soft medium, said predetermined propagation directions comprising at least two directions forming between them an angle different from 0 degrees and different from 180 degrees, said ultrasonic observation transducers being positioned at least along said predetermined propagation directions so that a complete measurement of the anisotropic soft medium is obtained within a period of less than 50 ms, each transducer emitting simultaneously while obtaining the measurement;

wherein the at least one shear wave is generated from a central axis perpendicular to the outer surface of the anisotropic soft medium and measurement points where passing of the at least one shear wave is detected, are each located at a distance from said central axis of less than 2 cm, wherein the at least one shear wave is generated by having an ultrasonic excitation transducer bearing said ultrasonic observation transducers emit an ultrasonic excitation wave focused on the central area, which displaces the anisotropic soft medium along said central axis, wherein the at least one shear wave is generated over a certain range of depths in the anisotropic soft medium and the propagation of said at least one at least one shear wave is observed at different depths inside said range of depths, and wherein the propagation of said at least one at least one shear wave is simultaneously observed in all of said predetermined propagation directions, with all the ultrasonic observation transducers;

(b) determining at least one propagation parameter of the at least one shear wave from data collected during (a) in each of said predetermined propagation directions;

wherein said at least one propagation parameter of the at least one shear wave is determined in each of said predetermined propagation directions at said different depths; and (c) characterizing at least one propagation parameter of the at least one shear wave, determined in each of the propagation directions in (b), and determining at least one rheological characteristic of the anisotropic soft medium, said at least one rheological characteristic being selected from the group consisting of a direction of the fibers of the anisotropic soft medium, a rheological elasticity parameter in a direction perpendicular to the fibers and a rheological elasticity parameter in the direction of the fibers, and wherein at least one rheological characteristic is determined at said different depths.

20. The method for characterizing an anisotropic soft medium according to claim 19 wherein said ultrasonic observation transducers are equidistributed on a circle centered on the central axis.

21. A method for characterizing an anisotropic soft medium comprising at least one portion including fibers and having a central area and an outer surface, said method comprising:

(a) obtaining a measurement by generating at least one shear wave which propagates by diverging from the central area, wherein propagation of said at least one shear wave is observed with ultrasonic observation transducers, from the outer surface of the anisotropic soft medium, in at least two predetermined propagation directions from said central area by maintaining fixed the ultrasonic observation transducers in relation to the anisotropic soft medium, said predetermined propagation directions comprising at least two directions forming between them an angle different from 0 degrees and different from 180 degrees, said ultrasonic observation transducers being positioned at least along said predetermined propagation directions so that a complete measurement of the anisotropic soft medium is obtained within a period of less than 50 ms;

wherein the at least one shear wave is generated over a certain range of depths in the anisotropic soft medium and the propagation of said at least one shear wave is observed at different depths inside said range of depths, wherein the at least one shear wave is generated from a central axis perpendicular to the outer surface of the anisotropic soft medium and measurement points where passing of the at least one shear wave is detected, are each located at a distance from said central axis of less than 2 cm, wherein the at least one shear wave is generated by having an ultrasonic excitation transducer bearing said ultrasonic observation transducers emit an ultrasonic excitation wave focused on the central area, which displaces the anisotropic soft medium along said central axis; and wherein the propagation of said at least one shear wave is simultaneously observed in all of said predetermined propagation directions, with all the ultrasonic observation transducers;

(b) determining at least one propagation parameter of the at least one shear wave from data collected during (a) in each of said predetermined propagation directions;

wherein said at least one propagation parameter of the at least one shear wave is determined in each of said predetermined propagation directions at said different depths; and (c) characterizing at least one propagation parameter of the at least one shear wave, determined in each of the propagation directions in (b), wherein at least one rheological characteristic of the anisotropic soft medium is determined, said at least one rheological characteristic being selected from the group consisting of a direction of the fibers of the anisotropic soft medium, a rheological elasticity parameter in a direction perpendicular to the fibers and a rheological elasticity parameter in the direction of the fibers;

wherein, during (a), the propagation of said at least one shear wave is simultaneously observed in all of said predetermined propagation directions, with all the ultrasonic observation transducers at the same time; and wherein a number of ultrasonic observation transducers is between 3 and 20.

22. The method for characterizing an anisotropic soft medium according to claim 21 wherein said ultrasonic observation transducers are equidistributed on a circle centered on the central axis.

23. A method for characterizing an anisotropic soft medium comprising at least one portion comprising fibers and having a central area and an outer surface, said method comprising:

(a) measuring by generating at least one shear wave which propagates by diverging from the central area in the anisotropic soft medium, wherein propagation of said at least one shear wave is observed in at least two predetermined propagation directions with ultrasonic observation transducers, from the outer surface of the anisotropic soft medium, said ultrasonic observation in at least two predetermined propagation directions from said central area occurring by maintaining fixed the ultrasonic observation transducers in relation to anisotropic soft medium, said predetermined propagation directions comprising at least two directions forming between them an angle different from 0 degrees and different from 180 degrees, said ultrasonic observation transducers being positioned along said at least two predetermined propagation directions so that a complete measurement is carried out within a period of less than 50 ms, wherein the at least one shear wave is generated from a central axis perpendicular to the outer surface of the anisotropic soft medium and measurement points where passing of the at least one shear wave is detected, are each located at a distance from said central axis of less than 2 cm wherein the at least one shear wave is generated by having an ultrasonic excitation transducer bearing said ultrasonic observation transducers emit an ultrasonic excitation wave focused on the central area, which displaces the anisotropic soft medium along said central axis, wherein the at least one shear wave is generated over a certain range of depths in the anisotropic soft medium and the propagation of said at least one shear wave is observed at different depths inside said range of depths,
wherein said ultrasonic observation transducers are equi-distributed on a circle centered on the central axis, and
wherein the propagation of said at least one shear wave is simultaneously observed in all of said predetermined propagation directions, with all the ultrasonic observation transducers;
(b) determining at least one propagation parameter of the at least one shear wave from data collected during said measurement in each of said predetermined propagation directions,
wherein said at least one propagation parameter of the at least one shear wave is determined in each of said predetermined propagation directions at said different depths; and
(c) characterizing at least one propagation parameter of the at least one shear wave, determined in each of said predetermined propagation directions,
wherein at least one rheological characteristic of the anisotropic soft medium is determined, said at least one rheological characteristic being selected from the group consisting of a direction of the fibers of the anisotropic soft medium, a rheological elasticity parameter in a direction perpendicular to the fibers and a rheological elasticity parameter in the direction of the fibers, and
wherein at least one rheological characteristic is determined at said different depths.

24. A method for determining at least one rheological characteristic of an anisotropic soft medium comprising at least one portion comprising fibers and having a central area and an outer surface, said method comprising:
(a) obtaining a measurement by generating at least one shear wave which propagates by diverging from the central area, wherein propagation of said at least one shear wave is observed with ultrasonic observation transducers, from the outer surface of the anisotropic soft medium, in at least two predetermined propagation directions from said central area by maintaining fixed the ultrasonic observation transducers in relation to the anisotropic soft medium, said predetermined propagation directions comprising at least two directions forming between them an angle different from 0 degrees and different from 180 degrees, said ultrasonic observation transducers being positioned at least along said predetermined propagation directions so that a complete measurement of the anisotropic soft medium is obtained within a period of less than 50 ms, each transducer emitting simultaneously while obtaining the measurement;
wherein the at least one shear wave is generated from a central axis perpendicular to the outer surface of the anisotropic soft medium and measurement points where passing of the at least one shear wave is detected, are each located at a distance from said central axis of less than 2 cm,
wherein the at least one shear wave is generated by having an ultrasonic excitation transducer bearing said ultrasonic observation transducers emit an ultrasonic excitation wave focused on the central area, which displaces the anisotropic soft medium along said central axis,
wherein the at least one shear wave is generated over a certain range of depths in the anisotropic soft medium and the propagation of said at least one shear wave is observed at different depths inside said range of depths,
wherein said ultrasonic observation transducers are equi-distributed on a circle centered on the central axis, and
wherein the propagation of said at least one shear wave is simultaneously observed in all of said predetermined propagation directions, with all the ultrasonic observation transducers;
(b) determining at least one propagation parameter of the at least one shear wave from data collected during said measurement in each of said predetermined propagation directions,
wherein said at least one propagation parameter of the at least one shear wave is determined in each of said predetermined propagation directions at said different depths; and
(c) characterizing at least one propagation parameter of the shear wave, determined in each of said predetermined propagation directions,
wherein said at least one rheological characteristic is selected from the group consisting of a direction of the fibers of the anisotropic soft medium, a rheological elasticity parameter in a direction perpendicular to the fibers, and a rheological elasticity parameter in the direction of the fibers,
wherein said at least one rheological characteristic is determined at said different depths, and
wherein during (a), the at least one shear wave is generated from a central axis, and during (c), an ellipsoidal curve $C(V(\Theta)\cdot\cos\Theta, V(\Theta)\cdot\sin\Theta)$ is determined by interpolation according to propagation parameters values computed at (b) in said predetermined propagation directions, wherein $V(\Theta)$ is a value of the propagation parameter in a plane perpendicular to said central axis and $\Theta$ is an angle designating a propagation direction in said plane with respect to a reference system belonging to said plane, the direction of the fibers corresponding to an angle $\Theta_0$ corresponding to a maximum of $V(\Theta)$, the rheological elasticity parameter in the direction of the fibers being determined according to $V(\Theta_0)$ and the rheological elasticity parameter in the direction perpendicular to the fibers being determined according to $V(\Theta_0+\pi/2)$.

* * * * *